(12) United States Patent
Downs et al.

(10) Patent No.: US 8,026,407 B2
(45) Date of Patent: Sep. 27, 2011

(54) ANTIMICROBIAL COMPRESSION BANDAGE

(75) Inventors: Suzanne A. Downs, Ho-Ho-Kus, NJ (US); Minh Quang Hoang, Sandy, UT (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 11/461,637

(22) Filed: Aug. 1, 2006

(65) Prior Publication Data
US 2008/0033329 A1 Feb. 7, 2008

(51) Int. Cl.
*A61F 13/00* (2006.01)

(52) U.S. Cl. .................. 602/48; 602/41; 602/44

(58) Field of Classification Search .......... 602/48, 602/75–77, 41–43; 604/304–308; 424/443–449
See application file for complete search history.

(56) References Cited

U.S. PATENT DOCUMENTS

| | | | |
|---|---|---|---|
| 3,061,469 A | 10/1962 | Manowitz et al. ......... 117/138.5 |
| 3,072,534 A | 1/1963 | Somerville et al. ............ 167/84 |
| 3,116,207 A | 12/1963 | Mulinos ......................... 167/84 |
| 3,547,688 A | 12/1970 | Gagliardi et al. .......... 117/138.5 |
| 3,959,556 A | 5/1976 | Morrison ..................... 428/364 |
| 4,307,717 A | 12/1981 | Hymes et al. ................ 128/156 |
| 4,343,853 A | 8/1982 | Morrison ..................... 428/233 |
| 4,377,160 A | 3/1983 | Romaine ...................... 128/156 |
| 4,578,066 A | 3/1986 | O'Connor .................... 604/366 |
| 4,736,467 A | 4/1988 | Schwarze et al. ................ 2/114 |
| 4,784,909 A | 11/1988 | Emi et al. ..................... 428/357 |
| 4,855,139 A | 8/1989 | Srinivasan .................... 424/404 |
| 5,006,401 A | 4/1991 | Frank ........................... 428/231 |
| 5,051,256 A | 9/1991 | Barnes et al. ................. 424/402 |
| 5,091,102 A | 2/1992 | Sheridan ......................... 252/91 |
| 5,093,359 A | 3/1992 | Szilagi et al. ................. 514/450 |
| 5,215,815 A | 6/1993 | Levy ............................ 428/246 |
| 5,290,269 A | 3/1994 | Heiman ........................ 604/378 |
| 5,297,296 A | 3/1994 | Moretz et al. ..................... 2/237 |
| 5,503,840 A | 4/1996 | Jacobson et al. ............. 424/421 |
| 5,856,248 A | 1/1999 | Weinberg ..................... 442/118 |
| 6,009,559 A | 1/2000 | Sesselmann .................. 2/243.1 |
| 6,096,334 A | 8/2000 | Rolf et al. .................... 424/443 |
| 6,120,784 A | 9/2000 | Snyder, Jr. ................... 424/404 |
| 6,194,332 B1 | 2/2001 | Rock et al. ................... 442/312 |
| 6,197,315 B1 * | 3/2001 | Beerse et al. ................ 424/401 |
| 6,312,705 B1 | 11/2001 | Gottlund et al. ............. 424/404 |
| 6,355,858 B1 | 3/2002 | Gibbins .......................... 602/41 |
| 6,479,144 B2 | 11/2002 | Petrea et al. ................. 428/379 |
| 6,602,811 B1 | 8/2003 | Rock et al. ................... 442/312 |
| 6,605,751 B1 | 8/2003 | Gibbins et al. ................. 602/41 |
| 6,700,032 B1 | 3/2004 | Gray ............................... 602/48 |

(Continued)

FOREIGN PATENT DOCUMENTS

WO  WO 9732613 A1 * 9/1997

(Continued)

OTHER PUBLICATIONS

Cliff Gromer, "Smart Threads," *Popular Mechanics* (Apr. 2004).

*Primary Examiner* — Kim Lewis
(74) *Attorney, Agent, or Firm* — Lisa P. Fulton (57) ABSTRACT

An antimicrobial material suitable for use in a compressive bandage is provided. Also, a composition that is used to produce this material and the methods for production are provided.

10 Claims, 2 Drawing Sheets

U.S. PATENT DOCUMENTS

| | | | |
|---|---|---|---|
| 6,755,052 B1 | 6/2004 | Sytz | 66/196 |
| 6,794,555 B2 | 9/2004 | Apert et al. | 602/48 |
| 6,821,936 B2 | 11/2004 | Green et al. | 510/319 |
| 2002/0127402 A1 | 9/2002 | Green et al. | 428/377 |
| 2002/0146950 A1 | 10/2002 | Reich | 442/96 |
| 2003/0091616 A1 | 5/2003 | Phaneuf et al. | 424/443 |
| 2003/0118631 A1 | 6/2003 | Xing et al. | 424/446 |
| 2004/0121682 A1 | 6/2004 | Quincy et al. | 442/123 |
| 2004/0166143 A1 | 8/2004 | Last et al. | 424/443 |
| 2004/0166753 A1 | 8/2004 | Millward et al. | 442/123 |
| 2004/0168426 A1 | 9/2004 | Shigemura | 57/225 |
| 2004/0171323 A1 | 9/2004 | Shalaby | 442/123 |
| 2004/0202700 A1 | 10/2004 | Phaneuf et al. | 424/443 |
| 2005/0027219 A1 | 2/2005 | Schultze et al. | 302/3 |
| 2007/0240247 A1 * | 10/2007 | Beck | 2/16 |

FOREIGN PATENT DOCUMENTS

| | | | |
|---|---|---|---|
| WO | WO 9818330 A1 * | 5/1998 | |
| WO | WO 9927792 A1 * | 6/1999 | |

* cited by examiner

ANTIMICROBIAL COMPRESSION BANDAGE

BACKGROUND OF THE INVENTION

Field of the Invention

This invention relates to a compression bandage having antimicrobial properties and the method of making this bandage.

Many bodily injuries, particularly those that are commonly referred to under the broad designation of contusions, are painful and cause substantial discomfort to the injured person due to the tissue damage and the resulting hemorrhaging of blood beneath the skin, which in turn causes substantial swelling. Swelling causes the injury to be more painful and disabling. It has long been recognized that, if the swelling can be minimized, the pain and discomfort can also be minimized or even eliminated. For this purpose, it has been conventional practice to apply ice packs or similar devices to the injured portion of the body as soon as possible after the injury occurs in an attempt to minimize swelling. This technique, however, is conveniently usable only under specific situations and circumstances. For example, ice packs and the like can be conveniently applied only to certain types of injuries, and use of such ice packs normally does not permit application of proper compression on and around the injured area so as to achieve the best possible minimization of swelling. Further, when an ice pack is applied, the injured person has little freedom of movement.

Alternatively, a compression bandage can be quickly and easily wrapped around an injured portion of the body, such as a body part that has suffered a contusion, to minimize subsequent swelling of the body in the region of the injury. Such bandage can be used to apply proper compression on and around the injured body portion, as well as permit cooling of the injured body portion due to both refrigeration and evaporation. This bandage can be clean and non-toxic and can be constructed such that it does not stick or adhere to the skin so that the bandage can be easily unwrapped from the injured body portion without causing discomfort or requiring any cleaning of the skin.

Woven elastic compression bandages have long been used in the treatment of humans and animals. Such bandages are stretchable in a longitudinal direction to about twice their relaxed length and are applied by being wrapped in a stretched condition around that part of the patient's body being treated, i.e., appendage, trunk, etc.

Several general types of woven elastic compression bandages have been available. In one type, the contraction power is provided by warp yarns of elastomeric material, such as rubber, the "Spandex" material available from E. I. duPont de Nemours and Co., or the like. In the other type, the contraction power is provided by warps formed from "stretch" yarns of such materials as nylon. These latter yarns get their primary stretch characteristics from configurational aspects (e.g., crimps or the like) of the individual filaments that make up the multifilament yarn ends.

Woven elastic bandages relying upon elastomeric materials for their stretchability qualities typically have elastomeric warp yarns located at intervals across the width of the woven fabric, with inelastic warp yarns (e.g., cotton yarns) disposed in the zones between the elastomeric warp yarns. In one such construction, the elastomeric warp yarns are interwoven with weft yarn picks in a 1×1 weave and the cotton warp yarns are interwoven with the weft yarn picks in a 2×2 weave.

The bandage may be packaged in a small and compact form, stored and reused. However, as the bandage is worn, it can collect bacteria through contact with the skin and perspiration, which can lead to an unpleasant odor, requiring the bandage to be washed. This is both inconvenient and undesirable. Furthermore, repeated washing is likely to shorten a useful life of the bandage.

The odor on the bandage material may be caused by various bacteria that can permeate and colonize on the material. Various antimicrobial materials are known.

U.S. Pat. No. 3,072,534 relates to the finishing of cellulosic textile materials, including fibers and articles formed therefrom, using neomycin. The materials suitable for treatment and the required presence of neomycin limit the type and ability of antimicrobial treatment. Furthermore, the antimicrobial compositions disclosed in the patent utilize metal ions.

U.S. Pat. No. 3,116,207 relates to a method of protecting textiles against the action of noxious organisms, such as fungi and bacteria, which protection is retained after repeated washing and cleaning operations.

U.S. Pat. No. 3,547,688 discloses microbiocidal compositions, which are prepared by complexing water-soluble biocidal metal salts with arizadinyl compounds to form solutions containing arizadinyl metal adducts. These solutions are then applied onto a fabric.

U.S. Pat. No. 3,959,556 relates to composite antimicrobial yarns comprising an intimate admixture of naturally occurring fibers and synthetic fibers. The antimicrobial composition is added to the raw materials prior to forming the fiber. It is disclosed that a part of the antimicrobial agent migrates to the surface of the fiber. However, since the antimicrobial composition is added prior to fiber formation, a large amount of the antimicrobial must be used in order to achieve the desired results.

U.S. Pat. No. 4,343,853 relates to a fabric construction having a backing fabric and a face fabric. At least one of the fabrics is made at least in part of yarns formed from synthetic fibers, which have incorporated thereunto an antimicrobial agent. In some embodiments, a tie yarn joins the two faces in plated relation. Even with minimal contact of the yarns in the two fabrics, the antimicrobial agent is said to migrate from within the treated fibers in the one fabric to the surface thereof and transfers to the yarns in the other fabric. Thus, it is purported that there is imparted antimicrobial protection to both fabric faces while maintaining the advantages of naturally occurring, untreated fibers in one of the fabrics. Again, since the antimicrobial composition is added prior to fiber formation, a large amount of the antimicrobial must be used in order to achieve the desired results, particularly if migration to other fibers is required.

U.S. Pat. No. 5,856,248 relates to cellulose fibers and products comprising treated fibers to absorb body secretions and to substantially decrease microbial growth. The fibers are chemically treated with a water-soluble salt of a transition metal and an alkali and, after this, with a solution of a bisbiguanide compound, forming a bond between the fibers, the transition metal and the bisbiguanide. Since this patent requires the use of a cellulosic material to achieve the desired effect, applicability of the antimicrobial treatment is very limited. Furthermore, the use of a water-soluble antimicrobial compound can lead to decreased durability during washing.

U.S. Pat. No. 5,297,296 discloses a multi-layer moisture management knitted elastic fabric. This fabric has two functionally distinct yet integrated layers; a moisture transport layer comprised of hydrophobic yarns and a second moisture dispersal layer comprised of hydrophilic yarns.

U.S. Pat. No. 6,479,144 discloses polyurethane elastomeric yarns, which incorporate antimicrobial agents in their formula. The agents are incorporated into the base polyurethane prior to spinning or extruding into a yarn or fiber, thereby incorporating the agent into a homogeneous filament.

U.S. Patent Application Publication No. 2005/0027219 A1 discloses a sleeve-knitted cast liner, which may be treated to have antimicrobial properties. This cast liner is designed not to absorb water.

U.S. Patent Application Publication No. 2002/0146950 A1 discloses antimicrobial materials comprised of polyester and an acetate fiber containing an antimicrobial. In order to attain durability during washing, the antimicrobial composition must be incorporated into the acetate prior to fiber formation. This process, however, is more expensive and requires a substantial amount of an antimicrobial composition to achieve the desired results.

While a number of developments have been made to provide a material with antimicrobial properties, there is still a need to provide an antimicrobial fibrous matrix, which is easy and inexpensive to produce, and which can be used to make a compressive bandage that requires fewer washing cycles and can retain its antimicrobial properties after repeated washing. Also, an antimicrobial composition, which can allow the production of such a material, is needed.

SUMMARY OF THE INVENTION

An object of the present invention is to provide a material having antimicrobial properties, which can be used as a compressive bandage and is easy and inexpensive to produce and which requires fewer washing cycles and can retain its antimicrobial properties after repeated washing.

Another object of the present invention is to provide an antimicrobial composition, which can be used to provide the antimicrobial material.

Yet another object of the present invention is to provide a method by which fibers may be treated to obtain the antimicrobial material.

An elastic antimicrobial material in accordance with the present invention comprises a synthetic elastic fiber woven with an absorbent fiber and at least one biocidal agent. The biocidal agent is applied to the fibers after they are formed, and the concentration of the biocidal agent on the material is from about 0.01 mg/cm$^2$ to about 0.1 mg/cm$^2$.

The antimicrobial composition in accordance with the present invention comprises at least 50 wt. % of at least one alcohol, based on a total weight of the antimicrobial composition, and at least one biocidal agent, which is not an alcohol. The composition is, preferably, in the form a non-aqueous alcohol solution. The composition can also include a polymer.

The antimicrobial composition can be applied to the fibers before or after that are weaved together to form the fabric. The application methods include dipping, spray drying, and pad or screen printing. Preferably, the fibers are dried after the application of the antimicrobial composition.

DETAILED DESCRIPTION

The present invention is related to a material that can be used to form a compressive bandage that contains at least one antimicrobial agent within the matrix of the bandage material. This invention also relates to the selection of a mixture of antimicrobial agent systems to provide a long lasting antimicrobial efficacy even after multiple washes.

The material is preferably produced in the form of an elastic strip. This strip is preferably significantly longer in its longitudinal dimension than in its width, so that it may be properly wrapped around a portion of the user's body. Typically, in its relaxed condition, the elastic strip of material may be about 36 inches (90 cm) long by about 6 inches (15 cm) wide. Of course, these dimensions are merely for illustration only and can be varied.

The pretreated fabric may, for example, be an ACE™ brand elastic bandage (ACE is a registered trademark of Becton, Dickinson and Company, Franklin Lakes, N.J.). Specific current ACE™ products in which the material in accordance with the present invention can be used include, but are limited to, ACE™ E-Z Clip (2, 3, 4 and 6 inch bandages); ACE™ Velcro Fastener (2, 3 and 4 inch bandages); ACE™ Self Adhering Athletic Bandage (2, 3 and 4 inch bandages; ACE™ Hot & Cold Compress; ACE™ Hot & Cold Compression Wrap; ACE™ Hot & Cold Combo Pack; ACE™ Ankle Brace—Woven (small, medium and large); ACE™ Knee Brace—Woven (small, medium and large); ACE™ Knee Brace with Side Stabilizers—Woven (small, medium and large); ACE™ Elbow Brace—Woven (small, medium and large); ACE™ Rigid Wrist Brace—Woven (small, medium and large); ACE™ Wrist Brace—Woven (one size); Tensor E-Z Clip (2, 3, 4 and 6 inch bandages); Tensor Velcro Fastener (2, 3 and 4 inch bandages); Tensor Self Adhering Athletic Bandage (2, 3 and 4 inch bandages); Tensor Hot & Cold Compress; Tensor Hot & Cold Compression Wrap; Tensor Ankle Brace—Woven (small, medium and large); Tensor Knee Brace—(small, medium and large); Tensor Knee Brace with Side Stabilizers—Woven (small, medium and large); Tensor Elbow Brace—Woven (small, medium and large); Tensor Rigid Wrist Brace—(small, medium and large); and Tensor Wrist Brace—Woven (one size).

The material in accordance with the present invention preferably has a stretch rate from about 150% to about 180%, more preferably from about 160% to about 175%. The return rate is preferably from about 100% to about 107%, more preferably from about 102% to about 106%. However, these characteristics can vary depending on the type of product that needs to be manufactured.

Although a separately applied adhesive can be used between the contacting surfaces of the bandage to obtain the adhesion after wrapping, it is preferred, for convenience in use, to make the opposite surfaces of the bandage self-adherent. It is preferred that the self-adherent properties of the bandage be such that the bond strength at the adhesive joint is less than the strength of the bandage itself in order that removal of the bandage will be achieved by adhesive bond failure at the adhesive joint, rather than cohesive failure of the material of which the bandage is made, in order that the bandage will not be destroyed when it is removed. For example, the bandage self-adherent properties can be achieved using Velcro®.

The biocidal agents are incorporated into the bandage material to control the growth of bacteria and to reduce the amount of bacteria that will colonize on the bandage during normal wear, as the bandage absorbs perspiration or comes in contact with skin flora. Due to a reduction in the colonization of odor causing bacteria, the bandage can remain fresher smelling when used. Therefore, the bandage should not need to be washed as often and can last for a longer period of time than the same bandage that was not treated with the antimicrobial.

Figure 1:
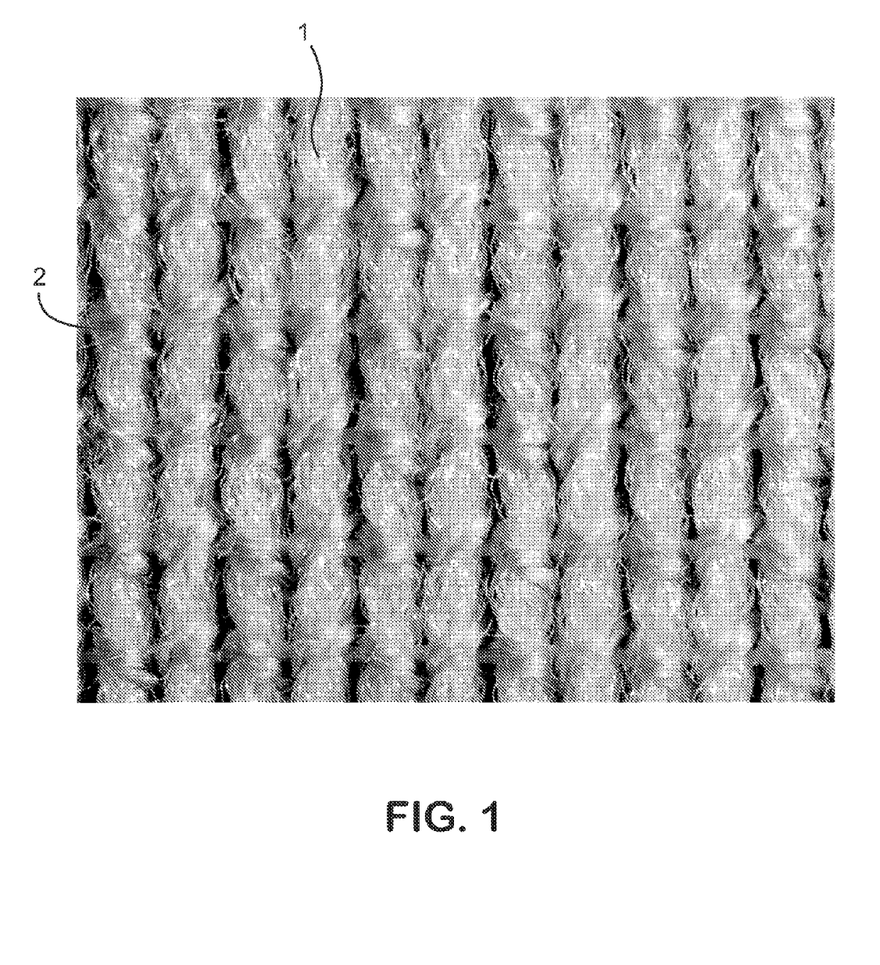
FIG. 1 is a microphotograph of a warp knit fabric stretched by about 15%.

The material for use in the present invention comprises woven, rather than knit, fibers. The differences between these two types of material are shown, for example, in FIGS. 1 and 2. FIG. 1 depicts a knit fabric. One set of fibers 1 (e.g., polyester) extend in a longitudinal direction and another set of fibers 2 (e.g., cotton/polyester/rubber tape) extend in a widthwise (horizontal) direction. This is a two-dimensional open knit arrangement of the fibers.

Figure 2:
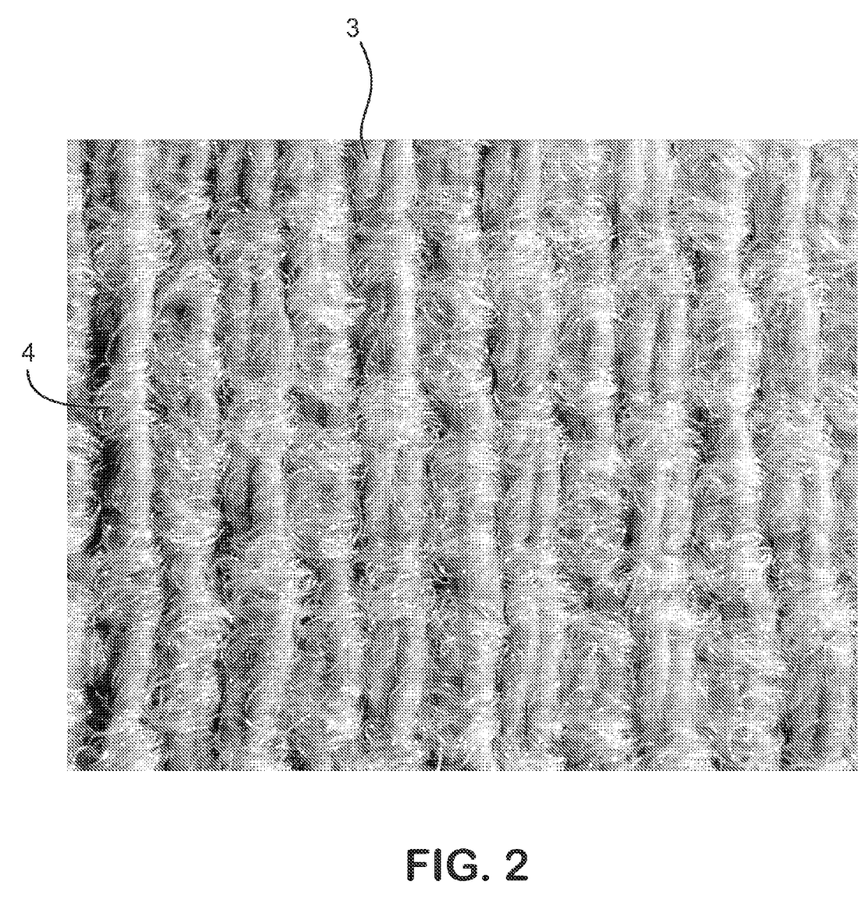
FIG. 2 is a microphotograph of a woven fabric stretched by about 15%.

FIG. 2 shows a woven fabric. In FIG. 2, one set of fibers 3 (e.g., cotton/polyester/rubber) extend both in the longitudinal direction ("y"-direction), and in a direction to and away from the viewer ("z"-direction). Another set of fibers 4 (e.g., polyester) extend horizontally ("x"-direction), weaving in-between the "y" and the "z" fibers. This structure is a true three-dimensional fabric.

Thus, the woven structure of the material provides a three-dimensional matrix for holding the antimicrobial or biocidal agent(s), which leads to greater and longer-lasting antimicrobial efficacy than would a knit structure, which, as discussed and shown above, is two-dimensional arrangement.

Furthermore, importantly, the antimicrobial composition is applied to the fibers after they have already been formed in lieu of adding the antimicrobial agent(s) to the raw materials prior to formation of the fibers. This method of application allows a much smaller amount of the biocidal agent(s) to be used than would be needed if the agent(s) were to be added prior to fiber formation. For instance, the concentration of the biocidal agent(s) on the material after application need not be more than about 0.1 mg/cm$^2$. In fact, this concentration may be as little as about 0.01 mg/cm$^2$.

Applicants have surprisingly found that addition of the antimicrobial agent(s) to the fibers that form a woven, elastic fabric in accordance with the present invention results in a long-lasting antimicrobial efficacy even after multiple washes. Previously, it had been thought that such permanence cannot be achieved by a topical administration of an antimicrobial agent (see U.S. Patent Application Publication No. 2002/0146950 A1).

The biocidal agents in accordance with the present invention are substantially insoluble in water. Preferably, this solubility is less than about 15 mg/L, more preferably less than about 10 mg/L. Since the bandages are typically washed in warm water in laundry machines, the low solubility in water allows the antimicrobial to remain on the bandage material and to continue to provide antimicrobial efficacy for an extended period of time.

The incorporation of the biocidal agent in accordance with the present invention should not compromise the strength of the material onto which it is applied. Also, the antimicrobial should not reduce the gas permeation of this material.

The antimicrobial composition that is applied to the bandage material in accordance with the present invention preferably comprises one or more alcohols. Suitable alcohols include, for example, ethanol, isopropanol propanol, butanol or any combination of these alcohols. Preferably, this alcohol is a $C_1$-$C_6$ lower alcohol, such as ethanol or isopropanol. More preferably, the $C_1$-$C_6$ lower alcohol is a mixture of isopropyl alcohol and ethanol in a ratio of about 1:10 to about 1:1. The one or more alcohols are present in an amount of at least 50 wt. %, preferably from about 50 to about 95 wt. %, based on the total weight of the antimicrobial composition. The antimicrobial composition of the present invention can further include at least one antimicrobial or biocidal agent that is not an alcohol (as described above).

Preferably, the concentration of the antimicrobial agent(s) on the material after application is preferably from about 0.01 mg/cm$^2$ to about 0.1 mg/cm$^2$. More preferably, the concentration is from 0.02 mg/cm$^2$ about to about 0.05 mg/cm$^2$.

The terms "biocidal agent", "antimicrobial agent" and "biocide," as used herein, refer to an agent that destroys, inhibits or prevents the propagation, growth and multiplication of unwanted organisms. These terms are used interchangeably.

The term "organisms" includes, but is not limited to, microorganisms, bacteria, undulating bacteria, spirochetes, spores, spore-forming organisms, gram-negative organisms, gram-positive organisms, yeasts, fungi, molds, viruses, aerobic organisms, anaerobic organisms and mycobacteria.

Specific examples of such organisms include the fungi *Aspergillus niger, Aspergillus flavus, Rhizopus nigricans, Cladosporium herbarium, Epidermophyton floccosum, Trichophyton mentagrophytes, Histoplasma capsulatum*, and the like; bacteria, such as *Pseudomonas aeruginosa, Escherichia coli, Proteus vulgaris, Staphylococcus aureus, Staphylococcus epidermis, Streptococcus faecalis, Klebsiella, Enterobacter aerogenes, Proteus mirabilis*, other gram-negative bacteria and other gram-positive bacteria, mycobactin and the like, as well as yeasts, such as *Saccharomyces cerevisiae, Candida albicans*, and the like. Additionally, spores of microorganisms, viruses and the like are organisms within the scope of the present invention.

Biocidal agents suitable for use in the present invention include, but are not limited to, biocides, such as phenol, quaternary ammonium biocides, chlorine-releasing biocides, quinoline, quinaldinium, thiosemicarbazone, quinone, sulfa, carbamates, salicylamide, carbanilide, amide, guanide, amidine, chelate and imidazoline biocides.

Other suitable biocides that can be used in the present invention include, for example, acetic acid, benzoic acid, propionic acid, dehydroacetic acid, sulfurous acid, vanillic acid, esters of p-hydroxybenzoic acid, 2-bromo-2-nitropropan-1,3-diol, formaldehyde, glutaraldehyde, calcium hypochlorite, potassium hypochlorite, iodine (in various solvents), povidone-iodine, hexamethylenetetramine, noxythiolin, 1-(3-choroallyl)-3,5,7-triazo 1-azoniaadamantane chloride, taurolidine, taurultam, EDTA, N(5-nitro-2-furfurylidene)-1-amino-hydantoin, 5-nitro-2-furaldehyde semicarbazone, 3,4,4'-trichlorocarbanilide, 3,4',5-tribromosalicylanilide, salicylanilide, 3-trifluoromethyl-4,4'-dichlorocarbanilide, 8-hydroxyquinoline, 1-cyclopropyl-6-fluoro-1,4-dihydro-4-oxo-7-(1-piperazinyl)-3-quinolinecarboxylic acid, 1,4-dihydro-1-ethyl-6-fluoro-4-oxo-7-(1-piperazinyl)-3-quinolinecarboxylic acid, hydrogen peroxide, peracetic acid, sodium oxychlorosene, parachlorometaxylenol, 2,4,4'-trichloro-2'-hydroxydiphenol, silver sulfadiazine and silver nitrate.

Additional suitable biocides include dyes, such as acridine, acriflavine, aminacrine hydrochloride, proflavin hemisulfate, triphenylmethane, magenta, crystal violet, scarlet red, pararosaniline, and rosaniline; chlorine releasing biocides, such as sodium hypochlorite, oxychlorosene, chloramine, dichlorodimethylhydantoin, halazone, dichloramine, chlorasine, succinchlorimide, trichloroisocyanuric acid, dichloroisocyanurate, trichloromelamine, dichloroglycoluril, halogenated dialkyl-hydantoin, and halane; quinaldinium and quinoline biocides, such as dequalinium, laurolinium, hydroxyquinoline, lioquinol, chlorquinaldol, halquinol, aminoquinuride, benzoxiquine, broxyquinoline, chloroxine, cloxyquin, ethylhydrocupreine, euprocin, hydrastine, 8-hydroxyquinoline, 8-hydroxyquinoline sulfate and iodochlorhydroxyquin; quaternary ammonium biocides, including pyridinium biocides, benzalkonium chloride, cetrimide, benzethonium chloride, cetylpyridinium chloride, chlorphenoctium amsonate, dequalinium acetate, dequalinium chloride, domiphen bromide, laurolinium acetate, methylbenzethonium chloride, myristyl-gamma-picolinium chloride, ortaphonium chloride, and triclobisonium chloride; furans, such as griseofulvin, nitrofurfural, nitrofurazone, nitrofurantoin, furazolidone, furaltadone, 2-(methoxymethyl)-5-nitrofuran, nidroxyzone, nifuroxime and nifurzide; phenol biocides, such as chlorinated phenol, cresol, thymol, carvacol, acetomeroctol, fenticlor, chlorocresol, chloroxylenol, hexachlorophene, bisphenols, amylmetacresol, bithionol, chlorothymol, dichloroxylenol, chlorophene, p-chlorophenol, p-phenylphenol, trinitrophenol, dichlorobisphenol, bromochlorobisphenol, 1-napthyl salicylate, 2-napthyl salicylate, 2,4,6-tribromo-m-cresol, and 3',4',5-trichlorosalicylanilide; lactones, such as propiolactone.

Examples of other biocides suitable for use in the invention include chlorhexidine, chlorhexidine gluconate, chlorhexidine acetate, chlorhexidine hydrochloride, dibromopropamidine, halogenated diphenylalkanes, dibromsalan, metabromsalan, tribromsalan, carbanilide, salicylanilide, tetrachlorosalicylanilide, trichlorocarbanilide, propamidine isethionate, pentamidine, picloxydine, mendalamine, the acid addition and quaternary, methenamine mandelate, polyoxymethylene esters such as polyoxymethylene diester, polyoxymethylene diacetate and the like, and mixtures thereof.

Particularly preferred biocides include triclosan, chlorhexidine dihydrochloride, chlorhexidine gluconate, chlorhexidine acetate, chlorhexidine diacetate, triclosan, chloroxylenol, dequalinium chloride, benzethonium chloride, benzalkonium chloride and combinations thereof. Furthermore, preferably, the one or more biocidal agents are present in an amount of about 0.01-10 wt. %, more preferably about 0.01-5 wt. %, based on the total weight of the antimicrobial composition.

The antimicrobial composition can be applied to the bandage material using various methods, such as through printing (pad, screen) or using a solution bath. Furthermore, the antimicrobial composition can be applied to the fibers prior or subsequent to weaving.

For example, the antimicrobial agents may be applied as follows. The fabric of the bandage is dipped into or sprayed (e.g., ultrasonic spraying) with an antimicrobial solution containing a mixture of antimicrobial agents, such as chlorhexidine base, triclosan, chloroxylenol, hexachlorophene, resorcinol, phenol and the like. The fabric material is then treated to evaporate the solvent, for example, using heat, leaving the antimicrobial inside the polymer matrix of the fabric materials.

To further improve the long-lasting presence of the antimicrobial agents on the bandage material, a polymer can be included in the antimicrobial solution that is applied to the material. Specifically, when the material is soaked with or is dipped into this solution, and the solvent is evaporated during the heat treatment step, the antimicrobial agents are adhered to the fabric materials matrix by the polymer. The polymer helps to prevent the antimicrobial from being stripped off during washing. The polymers suitable for this application are, preferably, not soluble in water, but are soluble in alcohol, for example ethyl cellulose and the like. An acrylic polymer may also be used.

The antimicrobial compositions in accordance with the present invention can be prepared with simple mixing at room temperature. Typically, an alcohol and water, if used, will be mixed first, followed by the addition of the other ingredients, in any order. Table 1 lists specific examples of some of the antimicrobial compositions, which can be used in accordance with the present invention.

TABLE 1

| | Form. 1 (wt. %) | Form. 2 (wt. %) | Form. 3 (wt. %) | Form. 4 (wt. %) | Form. 5 (wt. %) | Form. 6 (wt. %) | Form. 7 (wt. %) | Form. 8 (wt. %) | Form. 9 (wt. %) |
|---|---|---|---|---|---|---|---|---|---|
| Ethyl alcohol | 70.00 | | 70.00 | 70.00 | | 70.00 | | | 70.00 |
| Isopropyl alcohol | | 70.00 | | | 70.00 | | 70.00 | 70.00 | |
| Triclosan | 1.00 | 1.00 | | 1.00 | 1.00 | 1.00 | | 1.00 | 1.00 |
| Chloroxylenol | | | 1.00 | | | | 1.00 | | |
| Chlorhexidine base | 0.10 | 0.10 | 0.10 | 0.10 | 0.10 | 0.10 | 0.10 | | |
| Acrylic polymer | | | | | 2.00 | 2.00 | 2.00 | | |
| Ethyl cellulose | | | | | | | | | 1.00 |
| Water | 28.90 | 28.90 | 28.90 | 28.90 | 26.90 | 26.90 | 26.90 | 29.00 | 28.00 |

Formulations 1-9 shown in Table 1 were prepared using the ingredients identified below in Table 2:

TABLE 2

| Ingredient | Supplier |
|---|---|
| Ethanol (190 proof) | VWR International, Inc. West Chester, Pennsylvania |
| Isopropyl Alcohol - (IPA) (>99% alcohol) | JT Baker Phillipsburg, New Jersey |
| Chlorhexidine Gluconate (20%) | Xttrium Laboratories Chicago, Illinois |
| Triclosan | Ciba Specialty Chemicals |
| Chloroxylenol | Clarien North Carolina |
| Ethyl Cellulose | The Dow Chemical Company Midland, Michigan |
| USP water | Becton Dickinson |
| Acrylic polymer | BF Goodrich Cleveland Ohio |

The following Examples are illustrative of the present invention.

Example 1

Three Ziplock® bags were brought to the lab. Each bag contained three different strips of ACE™ bandage or brace material. One strip was a section of Catalog number 207604 (ACE™ Bandage 4"—light beige), one strip was a section of Catalog number 207229 (ACE™ Nylon Ankle Brace—dark brown) and one strip was a section of Catalog number 207525 (ACE Elasto-prene Ankle Support—black color).

Each sample strip of material was cut into a multitude of 10 mm circles. One third of the samples of 10 mm circles were used as control samples, one third of the samples were test samples and were treated with a solution of 2% chloroxylenol in water, and one third of the samples were also test samples and were treated with a solution of 2% chloroxylenol in ethyl alcohol. The chloroxylenol solutions were applied by placing the 10 mm circle samples into the solution, removing the samples and then squeezing out the excess solution.

Petrie plates containing tripticase soy broth growth agar were inoculated with an organism. A sample of fabric was placed onto the surface in the center of the inoculated plate. The plate was covered and allowed to incubate overnight at 30° C. to 35° C. The distance between the sample and where the organism growth was apparent, i.e. the zone of inhibition, was then measured. The larger the distance between the sample and where the organisms began to grow around the sample, the greater the inhibition of the sample toward the organism, or the more efficacious the treated fabric.

The results are shown in Table 3.

TABLE 3

Zones of Inhibition (mm)

|  | P. aeruginosa | E. coli | C. albicans | S. aureus |
|---|---|---|---|---|
| Control Samples (no Chloroxylenol added to fabrics) | | | | |
| ACE ™ Elasto-prene Ankle Support | 0 | 0 | 0 | 0.5 |
| ACE ™ Bandage | 0 | 0 | 0 | 0.5 |
| ACE ™ Nylon Ankle Brace | 0 | 0 | 0 | 0 |
| Test Samples (solution of 2% Chloroxylenol in water added to fabric samples) | | | | |
| ACE ™ Elasto-prene Ankle Support | 0 | 2 | 1 | 5 |
| ACE ™ Bandage | 0.5 | 2 | 2 | 6 |
| ACE ™ Nylon Ankle Brace | 0 | 4 | 0.5 | 6 |
| Test Samples (solution of 2% Chloroxylenol in Ethyl alcohol added to fabric samples) | | | | |
| ACE ™ Elasto-prene Ankle Support | 0.5 | 2 | 0.5 | 4 |
| ACE ™ Bandage | 0 | 2 | 0.5 | 4 |
| ACE ™ Nylon Ankle Brace | 0 | 3 | 0.5 | 3.5 |

E. coli and S. aureus are the most common organisms found on human skin, with S. aureus making up almost 80% of the microorganisms. The test samples containing the chloroxylenol in solution with either water or ethyl alcohol showed significant inhibition and efficacy against both of these organisms compared to the control samples that did not contain the chloroxylenol solution. There is no significant difference between the test samples immersed in the chloroxylenol/water solution or the chloroxylenol/ethyl alcohol solution. Additionally, there is no significant difference between the materials tested in this experiment as all of the treated materials appear to inhibit the organisms.

Example 2

ACE™ bandages, Catalog Number 207604 (ACE™ Velcro Fastener—4 inch bandage), were oversprayed with a solution of Triclosan (1%), Isopropyl alcohol (70%) and water (29%) (Formula 8 in Table 1) using an ultrasonic sprayer. The amount of add-on of the antimicrobial agent was calculated to be 0.02 mg/cm$^2$. The treated bandage was divided into eleven equal samples. Sample one was left as is and not treated further. This is shown as the "no wash" sample in Tables 4-7 below. Sample two was washed with laundry detergent and warm water in a laundry cycle for 30 minutes and then air-dried in a clothes dryer for 20 minutes. This sample is labeled as "Wash 1" in Tables 4-7. The other samples were subsequently washed and dried for an additional 2-10 wash/dry cycles and labeled "Wash 2"-"Wash 10", respectively.

A sample of the bandage that had not been oversprayed with the antimicrobial solution was also used in this analysis and served as the control sample.

The following organisms were placed in trypticase soy broth and incubated overnight at 30° C. to 35° C.:
P. aeruginosa (ATCC #27853)
C. albicans (ATCC #10231)
E. coli (ATCC #25922)
S. aureus (ATCC #25923).

The overnight growths of the above organisms were spread evenly onto TSA plates. Four disks from each of the twelve samples (control, no wash and Wash 1-Wash 10) were placed on an agar plate that had been inoculated with one of the above organisms. This process was continued until each sample bag had four disks placed on agar plates for each of the organisms.

The plates were incubated overnight at 30° C. to 35° C. and then observed for zones of inhibition. The results of the observation are shown in Tables 4-7 below.

TABLE 4

Zones of Inhibition (mm) Challenged with P. aeruginosa

| Disk | 1 | 2 | 3 | 4 | Average |
|---|---|---|---|---|---|
| Control | 0 | 0 | 0 | 0 | 0 |
| No Wash | 0 | 0 | 0 | 0 | 0 |
| Wash 1 | 0 | 0 | 0 | 0 | 0 |
| Wash 2 | 0 | 0 | 0 | 0 | 0 |
| Wash 3 | 0 | 0 | 0 | 0 | 0 |
| Wash 4 | 0 | 0 | 0 | 0 | 0 |
| Wash 5 | 0 | 0 | 0 | 0 | 0 |
| Wash 6 | 0 | 0 | 0 | 0 | 0 |
| Wash 7 | 0 | 0 | 0 | 0 | 0 |
| Wash 8 | 0 | 0 | 0 | 0 | 0 |
| Wash 9 | 0 | 0 | 0 | 0 | 0 |
| Wash 10 | 0 | 0 | 0 | 0 | 0 |

TABLE 5

Zones of Inhibition (mm) Challenged with *C. albicans*

| Disk | 1 | 2 | 3 | 4 | Average |
|---|---|---|---|---|---|
| Control | 0 | 0 | 0 | 0 | 0 |
| No Wash | 1 | 1 | 1 | 1 | 1 |
| Wash 1 | 0 | 0 | 0 | 0 | 0 |
| Wash 2 | 0 | 0 | 0 | 0 | 0 |
| Wash 3 | 0 | 0 | 0 | 0 | 0 |
| Wash 4 | 0 | 0 | 0 | 0 | 0 |
| Wash 5 | 0 | 0 | 0 | 0 | 0 |
| Wash 6 | 0 | 0 | 0 | 0 | 0 |
| Wash 7 | 0 | 0 | 0 | 0 | 0 |
| Wash 8 | 0 | 0 | 0 | 0 | 0 |
| Wash 9 | 0 | 0 | 1 | 0 | 0 |
| Wash 10 | 0 | 0 | 0 | 0 | 0 |

TABLE 6

Zones of Inhibition (mm) Challenged with *E. coli*

| Disk | 1 | 2 | 3 | 4 | Average |
|---|---|---|---|---|---|
| Control | 0 | 0 | 0 | 0 | 0 |
| No Wash | 10 | 10 | 10 | 11 | 10 |
| Wash 1 | 8 | 8 | 9 | 8 | 8 |
| Wash 2 | 7 | 8 | 7 | 7 | 7 |
| Wash 3 | 8 | 7 | 7 | 7 | 7 |
| Wash 4 | 6 | 6 | 6 | 6 | 6 |
| Wash 5 | 5 | 6 | 5 | 5 | 5 |
| Wash 6 | 6 | 5 | 6 | 7 | 6 |
| Wash 7 | 6 | 7 | 7 | 7 | 7 |
| Wash 8 | 4 | 5 | 5 | 6 | 5 |
| Wash 9 | 4 | 3 | 3 | 3 | 3 |
| Wash 10 | 3 | 3 | 3 | 3 | 3 |

TABLE 7

Zones of Inhibition (mm) Challenged with *S. aureus*

| Disk | 1 | 2 | 3 | 4 | Average |
|---|---|---|---|---|---|
| Control | 2 | 2 | 1 | 3 | 2 |
| No Wash | 21 | 20 | 20 | 20 | 20 |
| Wash 1 | 16 | 16 | 17 | 16 | 16 |
| Wash 2 | 15 | 15 | 14 | 14 | 15 |
| Wash 3 | 14 | 14 | 13 | 14 | 14 |
| Wash 4 | 14 | 12 | 12 | 12 | 12 |
| Wash 5 | 12 | 12 | 14 | 12 | 12 |
| Wash 6 | 9 | 10 | 9 | 10 | 10 |
| Wash 7 | 10 | 11 | 11 | 12 | 11 |
| Wash 8 | 12 | 12 | 12 | 12 | 12 |
| Wash 9 | 10 | 11 | 10 | 11 | 11 |
| Wash 10 | 10 | 8 | 9 | 10 | 9 |

Bandages treated with a mixture of triclosan in isopropyl alcohol and water showed significant inhibition against *E. coli* and *S. aureus*. The efficacy of these bandages was maintained through ten wash and dry cycles.

These experimental results demonstrate various advantages of the present invention. For example, the solution of triclosan in isopropyl alcohol and water is efficacious against the two major organisms found on the surface of human skin. The method of application and the formula were sufficient to maintain efficacy through 10 wash/dry cycles. The three-dimensional nature of the woven bandage allows for a large amount of surface area to be in contact with the antimicrobial, insuring good inhibition. Importantly, these results were achieved with even an extremely small concentration of antimicrobial solution, i.e., 0.02 mg/cm$^2$.

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An elastic antimicrobial material comprising synthetic elastic fibers woven with absorbent fibers and at least one biocidal agent,
   wherein the at least one biocidal agent is applied to the fibers after they are formed and is adhered to the fibers by a polymer,
   wherein a concentration of the at least one biocidal agent on the fibers is from about 0.01 mg/cm$^2$ to about 0.1 mg/cm$^2$, and
   wherein the elastic antimicrobial material maintains antimicrobial efficacy after two wash/dry cycles.

2. The material according to claim 1, wherein the fibers are treated with an antimicrobial composition comprising an antimicrobial agent in a non-aqueous alcohol solution.

3. The material according to claim 1, having a stretch rate from about 150% to about 180% with a return rate from about 100% to about 107%.

4. The material according to claim 1, wherein the at least one biocidal agent is substantially insoluble in water.

5. The material according to claim 1, wherein the at least one biocidal agent is soluble in an alcohol.

6. The material according to claim 1, wherein the at least one biocidal agent is triclosan or chloroxylenol.

7. The elastic antimicrobial material of claim 1 wherein the polymer is selected from the group consisting of acrylic polymer and ethyl cellulose polymer.

8. The elastic antimicrobial material of claim 1 wherein the solubility of the biocidal agent in water is less than about 15 mg/L.

9. The elastic antimicrobial material of claim 8 wherein the solubility of the biocidal agent is less than about 10 mg/L.

10. The elastic antimicrobial material of claim 1 wherein the elastic antimicrobial material maintains antimicrobial efficacy after ten wash/dry cycles.

* * * * *

UNITED STATES PATENT AND TRADEMARK OFFICE
CERTIFICATE OF CORRECTION

PATENT NO.       : 8,026,407 B2
APPLICATION NO.  : 11/461637
DATED            : September 27, 2011
INVENTOR(S)      : Suzanne Downs Page 1 of 1

It is certified that error appears in the above-identified patent and that said Letters Patent is hereby corrected as shown below:

In the Specifications

Column 6
Line 41, delete "1-(3-choroallyl)" and insert -- 1-(3-chloroallyl) --, therefor.

Line 63, delete "lioquinol," and insert -- clioquinol, --, therefor.

Column 7
Line 10, delete "carvacol," and insert -- carvacrol, --, therefor.

Line 40 (Approx.), delete "mendalamine," and insert -- mandelamine, --, therefor.

Column 9
Line 8, delete "tripticase" and insert -- trypticase --, therefor.

Signed and Sealed this
Thirtieth Day of July, 2013

Teresa Stanek Rea
*Acting Director of the United States Patent and Trademark Office*